United States Patent [19]

Tepper

[11] Patent Number: 5,314,401
[45] Date of Patent: * May 24, 1994

[54] CONFORMABLE PEMF TRANSDUCER

[75] Inventor: John C. Tepper, Carrollton, Tex.

[73] Assignee: AMEI Technologies Inc., Wilmington, Del.

[*] Notice: The portion of the term of this patent subsequent to Mar. 23, 2010 has been disclaimed.

[21] Appl. No.: 677,665

[22] Filed: Mar. 29, 1991

[51] Int. Cl.$^5$ .............................................. A61N 1/00
[52] U.S. Cl. ......................................... 600/14; 600/15
[58] Field of Search ...................................... 600/9–15; 128/802, 804

[56] References Cited

U.S. PATENT DOCUMENTS

| | | | |
|---|---|---|---|
| 4,439 | 11/1926 | Birchall | 600/15 |
| 4,654,574 | 3/1987 | Thaler | 600/14 |
| 4,817,625 | 4/1989 | Miles | 128/782 |

Primary Examiner—Kyle L. Howell
Assistant Examiner—J. P. Lacyk
Attorney, Agent, or Firm—Baker & Botts

[57] ABSTRACT

A conformable PEMF transducer (FIG. 1a–1b) used for PEMF therapy (such as for healing non-union fractures of the hip). The transducer (FIG. 3) includes electrically conducting primary, secondary, and sense windings (31, 32, 33) formed into a transducer coil integral with non-conducting semi-rigid structural windings (34). The structural windings provide structural support for the coil so that it is formable into a selected anatomical contour, but still flexibly conformable to accommodate normal patient motion. Control electronics (FIG. 4) includes a PEMF processor (41) that executes a PEMF program for providing pulsing current to the front and back transducers at predetermined intervals, thereby activating the electromagnetic field according to a prescribed PEMF regimen.

23 Claims, 3 Drawing Sheets

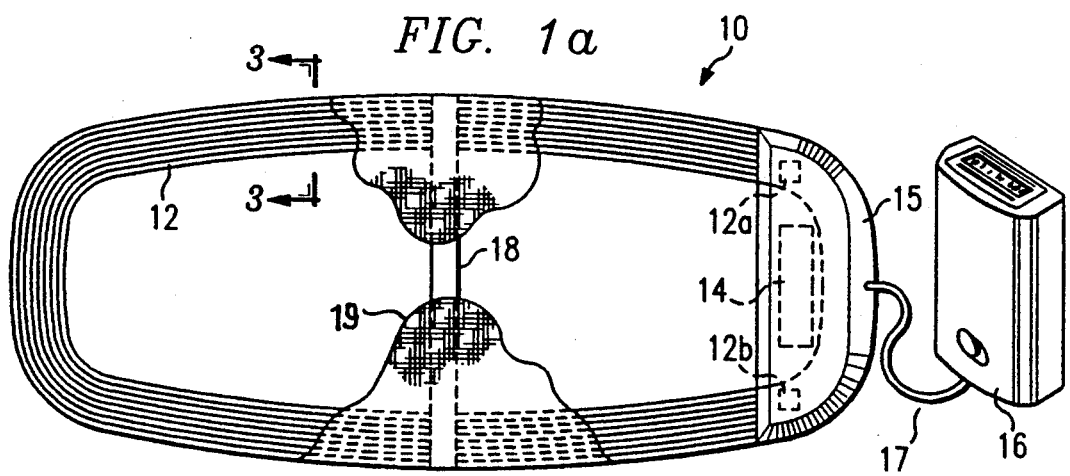
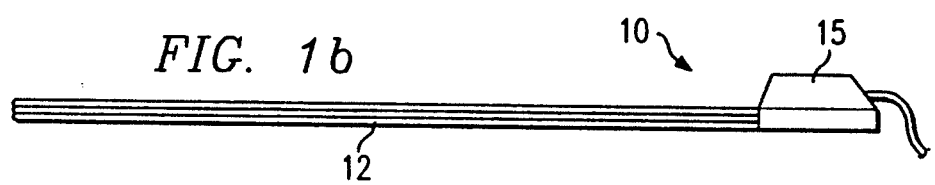
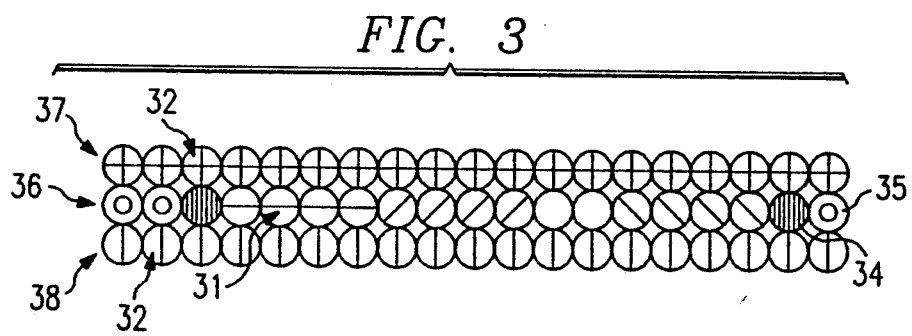
- ⊕ SECONDARY #1
- ⦶ SECONDARY #2
- ⊖ PRIMARY #1
- ⊘ PRIMARY #2
- ⊗ PRIMARY #3
- ○ SENSE
- ⊙ SPACER WINDING
- ▢ STRUCTURAL WINDING
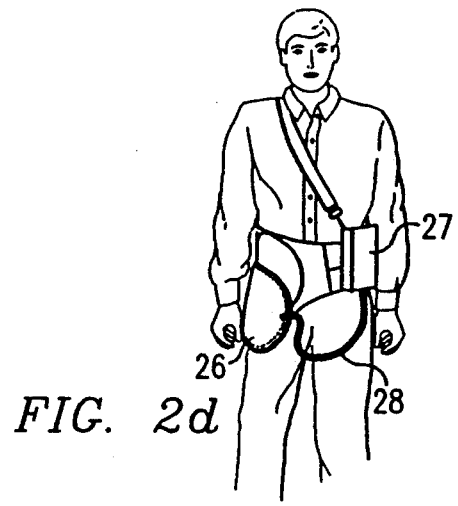

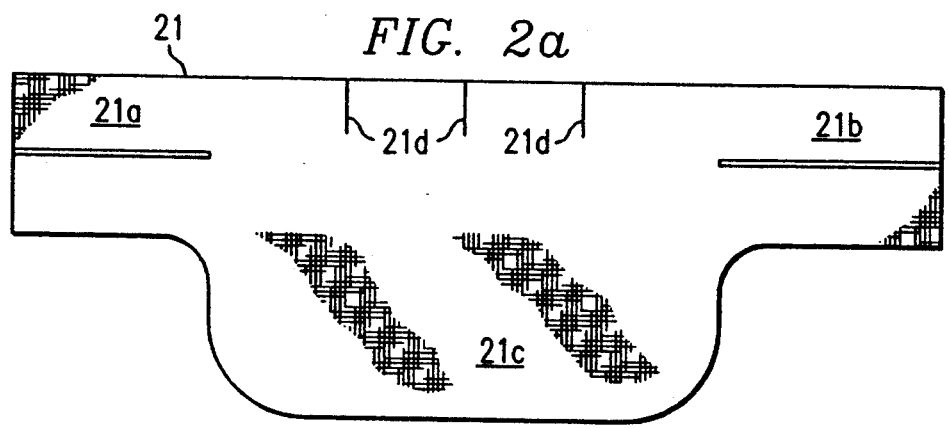
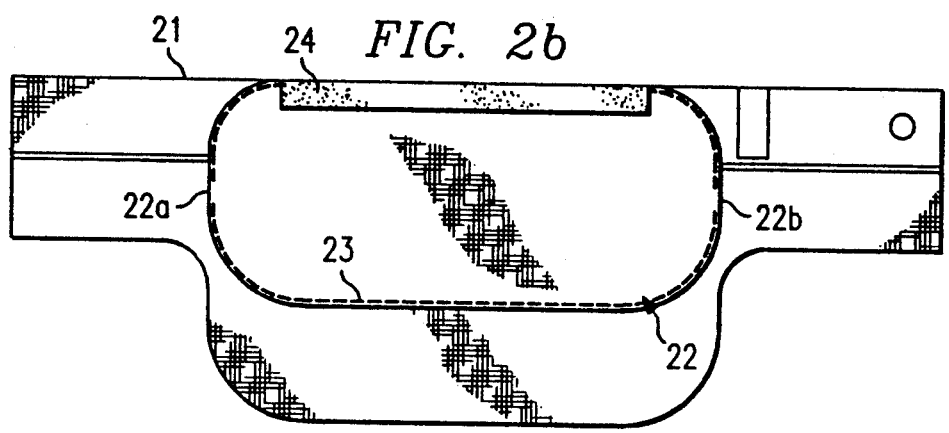
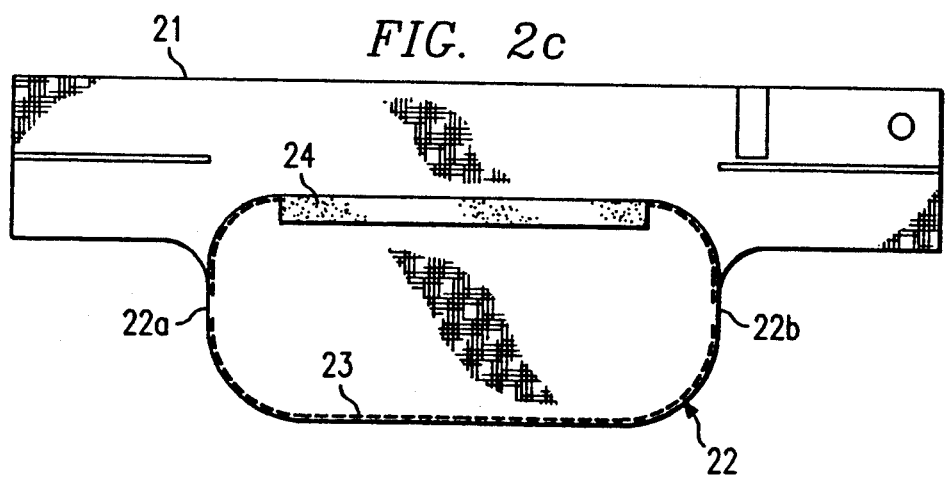

CONFORMABLE PEMF TRANSDUCER

TECHNICAL FIELD OF THE INVENTION

The invention relates generally to pulsed electromagnetic field (PEMF) therapy, and more particularly relates to a conformable PEMF transducer that, once formed to the anatomical contour of a selected area of a patient's body, is flexibly conformable to that contour to accommodate normal patient motion, and to a method of fabricating such a transducer. In even greater particularity, the conformable PEMF transducer is used to provide PEMF therapeutic stimulation to the hip area.

RELATED APPLICATION

This application is related to co-pending U.S. Pat. application Ser. No. 07/586,505 (Attorney Docket #90928-0090), titled Double-Transducer System for PEMF Therapy, which was filed on Sept. 21, 1990, and co-pending U.S. Pat. application Ser. No. 07/638,219 (Attorney Docket #90928-9991), titled Contoured Triangular Transducer System for PEMF Therapy, which was filed on Jan. 7, 1991, both of which are assigned to the assignee of this application.

BACKGROUND OF THE INVENTION

Pulsed electromagnetic fields (PEMF) are low-energy, time-varying magnetic fields that are used to treat therapeutically resistant problems of the musculo-skeletal system. Those problems include spinal fusion, ununited fractures, failed arthrodeses, osteonecrosis, and chronic refractory tendonitis, decubitus ulcers and ligament, tendon injuries, osteoporosis, and Charcot foot.

The specific problem to which the invention is applicable is the desirability, in certain application, of providing a PEMF transducer design that, while formable to a selected anatomical contour, is still flexibly conformable to accommodate normal patient movement. An example of an area where such conformability would be advantageous is the hip area, where there is a significant degree of anatomical variance between patients, and where a significant amount of movement occurs during normal patient activity.

For PEMF therapy, an electromagnetic transducer coil is placed over a selected area of the skeletal system such that pulsing the transducer produces an applied or driving field that penetrates to the target skeletal area. The conventional approach has been to use either a flexible or semi-rigid transducer construction.

The flexible transducer approach is disadvantageous in that the transducer cannot maintain a desired transducer configuration without some additional form of jacketing and/or strapping. Thus, while such transducers are flexibly conformable to patient movements, they cannot be formed to maintain a desired anatomical contour.

An alternative semi-rigid transducer construction is described in the related applications. Those applications teach a transducer construction in which the windings of the transducer coil are flat wound and bonded together, and then encased in a semi-rigid polyurethane elastomer shell that can be formed to a selected anatomical contour. While the degree of rigidity can be adjusted somewhat by the selection of a specific shell material, generally this type of construction does not provide sufficient flexible conformability to accommodate patient movements.

Accordingly, a need exists for a PEMF transducer construction that provides sufficient rigidity to be formable to a desired anatomical contour, but has sufficient conformability to accommodate normal patient movement.

SUMMARY OF THE INVENTION

The present invention is a conformable PEMF transducer that, once formed to a selected anatomical contour, is flexibly conformable to accommodate normal patient movement. In an exemplary application, the conformable PEMF transducer is configured for use in the hip area.

In one aspect of the invention, the conformable PEMF transducer includes at least a primary winding with a selected number of turns, and a structural winding of semi-rigid stiffening wire with a selected number of turns, bound together to form an integral transducer coil. The structural winding provides a predetermined degree of structural rigidity for the transducer, such that the transducer is formable to a selected anatomical contour and is flexibly conformable to accommodate patient movement.

Activation electronics are coupled to the primary winding for selectively generating electromagnetic fields to implement a prescribed PEMF therapy program (such as for non-union fractures and tightening loosened prostheses).

In an exemplary embodiment of the invention, the conformable PEMF transducer is used to provide PEMF therapy for the hip area. The transducer coil uses a flat-wound construction formed by three layers of a selected arrangement of conductive primary, secondary, and sense windings and non-conductive structural and spacer windings — the conductive windings are Mil-ene insulated wire, while the non-conductive structural winding is uninsulated 18 gauge copper wire. The degree of rigidity of the transducer coil is controlled by selecting the type and number of turns of structural wire, enabling the transducer to be formed into a desired anatomical contour, while being sufficiently flexible to permit conformability during normal patient movement.

The activation electronics includes separate control and drive electronics. A drive electronics circuit board is coupled to the primary, secondary and sense windings at one end of the transducer coil, and is encapsulated, along with the adjacent portions of the transducer coil, in a polyurethane shell. The control electronics are located in a separate control electronics module, along with a battery pack, and coupled to the drive electronics by a cable.

The control electronics includes a PEMF processor that executes a PEMF program for controlling the activation of the electromagnetic fields (field strength and duty cycle). In addition to implementing the PEMF therapy program, the PEMF processor collects appropriate data in memory to enable the attending health care professional to monitor the course of the therapy.

The drive electronics includes an energy recovery circuit — the secondary windings and the energy recovery circuit are active during a de-energization cycle to recover energy (conserving battery power). The secondary winding is also used to tailor the parameters of the electromagnetic field.

The exemplary conformable PEMF transducer coil is fabricated as follows. A central winding layer is formed by primary and sense windings, together with the structural and spacer windings, all wound around a flat mandrel and bound together with tape. Two outer winding layers are formed by secondary windings flat-wound on the same mandrel and bound together with tape. The two secondary winding layers are situated above and below the central winding layer, and the combined bundle is bound into an integral transducer coil by tape.

The technical advantages of the invention include the following. The non-conductive structural windings provide structural support and enable significant design control over the degree of flexibility, and therefore, conformability exhibited by the transducer coil. This transducer structure provides sufficient rigidity to be formable into a selected anatomical contour that will be retained under normal use. The transducer coil can be configured from flat-wound winding layers to provide a substantially flat cross sectional profile and a broad contact area. Programmable control electronics implement a PEMF program that provides appropriately controlled electromagnetic field activation in accordance with a predetermined PEMF therapeutic regimen, with storage of appropriate data for monitoring the progress of the PEMF therapy.

A more complete description of the invention, as well as further features and advantages, are provided by the Detailed Description of exemplary embodiments of the invention, read in conjunction with the accompanying Drawings. Although the Detailed Description and the Drawings are directed to specific exemplary embodiments, various modifications of these exemplary embodiments, as well as alternative embodiments, will be suggested to those skilled in the art, and it is to be understood that this invention encompasses any modifications or alternative embodiments that fall within the scope of the appended claims.

BRIEF DESCRIPTION OF THE DRAWINGS

FIGS. 1a and 1b respectively illustrate an exemplary conformable PEMF transducer coil, with encapsulated drive electronics and separate control electronics module, for the hip area;

FIGS. 2a-2d illustrate an exemplary foam belt with an attachable transducer pouch, with FIG. 2a illustrating the belt, FIGS. 2b and 2c respectively illustrating the belt with a pouch attached in an upper and lower position; and FIG. 2d illustrating the belt being worn by a patient.

FIG. 3 is an exemplary winding pattern for the transducer coil; and

DETAILED DESCRIPTION OF THE INVENTION

Figure 4:
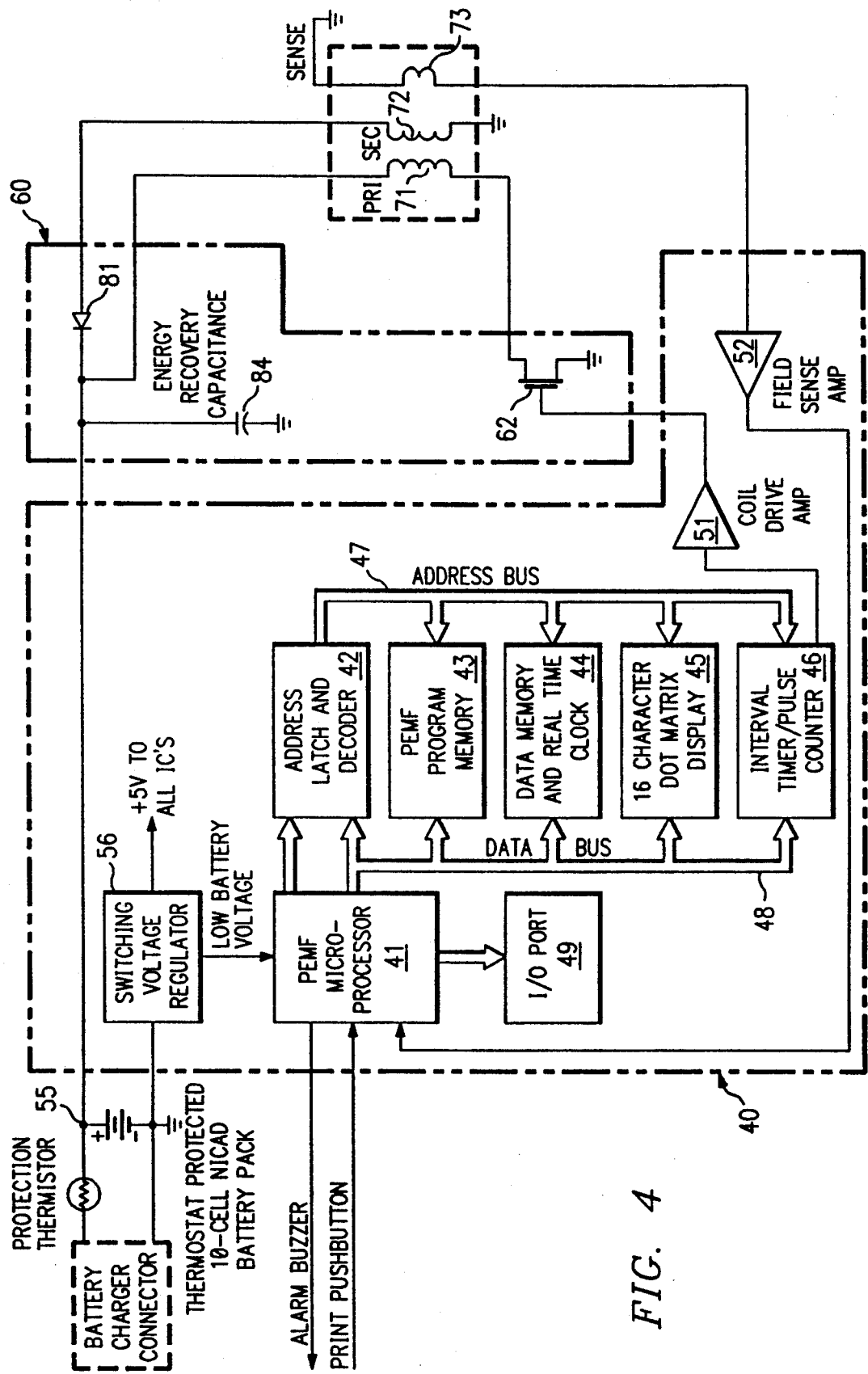
FIG. 4 is a schematic block diagram of the control electronics and the drive electronics.

The Detailed Description of an exemplary embodiment of the conformable PEMF transducer system is organized as follows:
1. Conformable Transducer
2. Hip Belt
3. Transducer Fabrication
4. Control and Drive Electronics The exemplary conformable PEMF transducer is used to provide PEMF therapeutic stimulation to the hip area, such as for healing non-union fractures and tightening loosened prostheses. However, the conformable PEMF transducer has general applicability to the design of PEMF transducer structures that are both formable into a selected anatomical contour, and are flexibly conformable to accommodate normal patient motion.

1. Conformable Transducer

FIGS. 1a-1b illustrate an exemplary conformable PEMF transducer system 10 that is designed to provide PEMF therapy to the hip area. The transducer system comprises three principal components: (a) a transducer coil 12 that is elongate and generally oval in shape; (b) encapsulated drive electronics 14 located at one end of transducer coil; and (c) a control electronics module 16 coupled to the drive electronics by a cable 17.

The transducer coil 12 is fabricated to be formable into a predetermined anatomical contour for positioning on the patient's hip. As described in Section 3, the transducer coil is fabricated with structural windings that provide sufficient structural rigidity to maintain the desired anatomical contour, while permitting sufficient flexibility for the transducer to be conformable under normal patient motion. The transducer may be formed into the desired anatomical contour by the manufacturer, or by a health care professional or patient.

A stay 18 may be included to provide lateral support for the elongated dimension of the transducer coil. The transducer coil except for the encapsulated end is covered by cloth material 19 (such as gortex).

The exemplary conformable transducer has a substantially flat cross sectional profile, which is a result of a flat-wound construction. As described in Section 3, the transducer coil includes conductive primary, secondary and sense windings, together with the structural windings of non-conducting stiffening wires.

To provide the desired electromagnetic fields for a prescribed PEMF therapy, the transducer coil includes both primary and secondary windings, with the secondary windings providing energy recovery, and as a collateral function, tailoring of the electromagnetic field output from the transducers. Alternatively, the advantages of the conformable PEMF transducer can be obtained using only a primary winding (i.e., with no energy recovery windings, but preferably with an alternative efficient programmed energy format).

Drive electronics 14 is incorporated onto a printed circuit board and encapsulated in a polyurethane shell 15 that covers one end of the transducer coil 12. The circuit board carrying the drive electronics is coupled to the primary, secondary and sense windings of the transducer coil, with the winding wires exiting the transducer coil bundle in the areas 12a and 12b.

The control electronics module 16 is carried by the patient by a shoulder strap (not shown), or alternatively by a belt. It includes a PEMF processor for providing pulsing current to the transducer coil at predetermined intervals, thereby activating the electromagnetic field according to a prescribed pre-programmed PEMF regimen.

For patient use, the conformable PEMF transducer is placed into a foam hip belt, including a pouch for the transducer, that secures the transducer in position on the patient's hip. The hip belt is described in Section 2.

To implement PEMF therapy program, a health care professional determines a PEMF therapy that includes a regimen of PEMF stimulation of the hip. The prescribed PEMF therapy regimen is translated into a PEMF program, which is programmed into a PEMF memory in the control electronics, either during manufacture or subsequently.

To commence a PEMF therapy session, the patient puts on the hip belt and secures the conformable PEMF transducer in place. The patient then starts the PEMF program by turning on the control electronics module.

In accordance with the stored PEMF therapy program, the PEMF processor correspondingly controls the activation current supplied to the transducer coil 12, thereby controlling the electromagnetic fields in terms of energization time, de-energization time, and duty cycle (repetition rate). In addition to controlling the PEMF therapy, the PEMF processor maintains treatment data that is available on request to the patient (through a small display), and to a health care professional (via an I/O port) for monitoring and analysis.

2. Hip Belt

FIGS. 2a–2d illustrate an exemplary hip belt for securing the conformable PEMF transducer in place on the patient's hip. The hip belt includes a foam belt to which is attached a transducer pouch for holding the transducer coil.

Referring to FIG. 2a, a belt 21 is formed from a foam material (such as Velfoam) that includes tabs 21a and 21b on either side of a pouch area 21c (to which a transducer pouch can be attached). The foam belt is confiqured to be worn on the hip, with the pouch area positioned over the hip area. To aid in fittinq, the foam belt 21 includes pleats 21d.

Referring to FIGS. 2b and 2c, the foam belt is shown with the a transducer pouch 22 attached, respectively, in an upper and lower position. The pouch includes on either end and opening 22a and 22b for the cable from the transducer coil to the control electronics module (see FIG. 2d). The pouch is attached by stitching 23 to the foam belt 21 in a selected position — high, low, or in between.

Once the pouch 22 is attached to the foam belt 21, the transducer coil (not shown) is inserted into the pouch through an opening 24 that can be sealed by a velcro fastener strip. The cable coupled to the drive electronics module is drawn out through one of the openings 22a/22b, and can then be attached to the control electronics module.

Referring to FIG. 2d, the hip belt 26 is worn around the patient's waist, with the transducer pouch arranged over the hip area. The control electronics module 27 is shown being carried by a strap, with a cable 28 coupling the control electronics module to the transducer (i.e., to the drive electronics).

3. Transducer Fabrication

For an exemplary embodiment, the conformable PEMF transducer is fabricated in a flat wound configuration as follows.

FIG. 3 is an enlarged cross sectional view of a transducer coil 30 illustrating an exemplary winding pattern. The transducer coil includes conductive primary 31, secondary 32 and sense 33 windings, together with structural 34 and spacer 35 windings.

The exemplary transducer coil construction includes three layers of windings. A center layer 36 includes the 12 primary and 2 sense windings, together with 2 structural and 3 spacer windings (which do not provide any significant structural support). Two separate outer layers 37 and 38 each are formed by 19 secondary windings. The degree of rigidity can be controlled by selecting the type of stiffening wire to use for the structural windings, and by selecting ratio of structural windings to spacer windings.

The primary, secondary and sense windings are 18 AWG (19 strand–30 AWG) tin plated copper conductor wires with a Mil-ene insulation. The structural windings are 18 AWG copper wire (uninsulated). The spacer windings are 0.057 inch diameter clear monofilament. The approximate dimensions of the winding bundle are 1.08 inches by 0.17 inches.

The winding pattern shown in FIG. 3 is exemplary only. Considerations involved in selecting a winding pattern include the efficient magnetic coupling between the primary and secondary windings, and the appropriate field strength.

For each layer, the appropriated windings are wound in a winding machine around a flat mandrel of the appropriate general shape for the transducer. The winding layer is maintained in the flat-wound position shown in FIG. 3 by parallel sideplates. Once wound, the start and finish wire ends for the winding layer are cut to provide leads for coupling to the drive electronics, and the windings are bound together with tape.

Once each of the three winding layers have been flat-wound and bound with tape, the two secondary winding layers 37 and 38 are placed on either side of the central winding layer, and this bundle is bound together with tape. The winding bundle is now a semi-rigid transducer coil, which includes integral structural windings that provide a selected degree of structural support. As a result, the transducer coil is formable into a selected anatomical contour, but remains sufficiently flexible to be conformable, accommodating normal patient motion.

Referring to FIGS. 1a and 1b, the next step is to position the drive electronics circuit board, indicated at 14, at one end of the transducer coil. The winding leads of the conductive primary, secondary, and sense windings of the transducer coil, and the lead wires of the cable 17, are connected to the drive electronics board.

The end of the transducer coil with the drive electronics board is placed in a mold of the appropriate shape, with the cable extending through a strain relief exit in the mold. A polyurethane-type elastomer or potting material is then introduced into the mold, encapsulating that end of the transducer coil, including the drive electronics board.

Alternatively, the encapsulating or potting material can be silicon rubber. The shore hardness should be 80 or less.

For the exemplary embodiment, a two component polyurethane elastomer is used: an isocyanate and a polyol. In a vacuum, the two components are mixed, and then poured into the mold, covering the end of the transducer coil and the drive electronics board. These steps are performed in a vacuum to eliminate entrapped air which can cause voids that reduce structural integrity and are cosmetically undesirable. The transducer coil and the mold are then placed in an oven for heat curing the polyurethane type elastomer material to form the encapsulating shell 15.

After cooling, the transducer coil is separated from the mold. The polyurethane is cleaned of mold release, and any flash is trimmed off.

Finally, the transducer is formed to the desired anatomical contour, such as by placing the coil in a bending fixture.

The completed semi-rigid transducer coil is now ready to be covered with cloth and inserted into the hip belt.

4. Control and Drive Electronics

FIG. 4 is a schematic block diagram of the control and drive electronics, which are physically located respectively in the control electronics module (16 in FIG. 1a) and within the encapsulated end of the transducer coil 12.

Control electronics 40 includes a PEMF processor 41, with associated IC (integrated circuit) components: an address latch and decoder circuit 42, a PEMF program memory 43, a data memory and real time clock circuit 44, a 4-character 7-segment display module 45 and an interval timer/pulse counter 46. The PEMF processor is coupled to these components by an address bus 47 and a data bus 48.

A PEMF program can be loaded into an EPROM or other memory and installed as PEMF program memory 43; alternatively, the PEMF program can be read into the PEMF program memory via an I/O port 49. Data collected during execution of the programmable PEMF program parameters — such as start time, stop time, duration, and daily average — is stored in the data memory 44, and can be read out to a printer (or over a communications link) via the I/O port 49.

The PEMF processor 41 and the interval timer/pulse counter 46 control a transducer drive amplifier 51. The coil drive amplifier controls the energization and de-energization of the transducer coil. A field sense amplifier 52 is used to sense the resulting electromagnetic fields, and provide an appropriate signal to the PEMF processor.

The PEMF processor 41 receives power from a power source, such as a NICAD battery pack 55, through a switching voltage regulator 56 (which also provides +5 volts power to the other IC components).

PEMF processor 41, and the supporting IC CMOS logic chips and display module, function conventionally and are commercially available. For the exemplary embodiment, PEMF processor 41 is an RCA 1806 processor. The address latch and decoder IC 42 is a type 1873. The PEMF program memory is a 2816 2 Kbyte EEPROM that is loaded with a PEMF program during manufacture. The data memory and real time clock IC 44 is a Mostek MK48T02, used to store representative data about the patient's use of the PEMF system based on the internally maintained clock and calendar. The 4-character, 7-segment display module 45 is a standard integrated display module package.

The interval timer/pulse counter IC 46 is an Intel 82C54 that includes two general purpose counters controlled by the PEMF processor, executing the PEMF program, to establish the duty cycle of the pulse output. The pulse output, in turn, controls the energization and de-energization of the transducers, and thereby determines the activation of the magnetic fields used in the PEMF therapy.

For the exemplary embodiment, the PEMF program causes the interval timer/pulse counter IC 46 to output a variable programmed train of, for example, 21 pulses lasting 5460 microseconds, with a pulse period of 65 microseconds on and 195 microseconds off. That is, for each pulse, the transducers are energized for 65 microseconds and then de-energized (recovery phase) for 195 microseconds. A pulse train is output to the transducers every 67,000 microseconds (every 67 milliseconds or one fifteenth of a second).

The pulse trains from the interval timer/pulse counter 46 are input to the transducer drive amplifier 51, which controls the drive electronics.

Drive electronics 60 controls activation of the transducer 70, and the generation of the PEMF fields. The transducer is represented by a primary winding 71, a secondary winding 72 and a sense winding 74.

Drive electronics 60 includes an FET switch 62 having its control gate coupled to the control electronics, specifically transducer drive amplifier 51. The FET switch controls the activation current through the primary windings 71, thereby controlling the energization and de-energization of the contoured triangular transducer.

When FET switch 62 is switched on (during a 65 microsecond on pulse), activation current from the battery 50 flows through the primary windings, energizing the transducer. When switched off (during the 195 microsecond off period), current flows through the secondary windings as the transducer is de-energized.

The other end of primary winding 71 is coupled back to the battery 55, as is the corresponding end of the secondary winding 72 through energy recovery diode 81 (the other end of the secondary winding is grounded). A parallel-coupled group of four energy recovery capacitors 84 release energy during transducer energization, and store energy during transducer de-energization. Thus, the energy recovery capacitors 84 and the diode 81 form an energy recovery circuit that operates in conjunction with the secondary winding to provide energy recovery, thereby conserving battery power.

The sense winding for the transducer is coupled back to the control electronics 40, and specifically through the field sense amplifier 52 to the PEMF processor 41. The field sense amplifier senses the electromagnetic fields generated during transducer activation, and provides feedback to the PEMF processor for monitoring the PEMF operation. The PEMF processor causes appropriate monitoring data to be stored in the data memory 44, and will cause an alarm signal in the case of malfunction.

What is claimed is:

1. A conformable PEMF transducer for providing PEMF therapeutic stimulation to a selected target area of a patient's body, comprising:
    a transducer including at least a primary winding with a selected number of turns, and a structural winding of semi-rigid stiffening wire with a selected number of turns to form a primary/structural winding bundle;
    said primary/structural winding bundle being held together to form an integral transducer coil, with the structural winding providing a predetermined degree of structural rigidity such that the transducer is formable to a selected anatomical contour and is flexibly conformable to accommodate patient movement; and
    activation electronics coupled to said primary winding for selectively activating electromagnetic fields, thereby implementing a prescribed PEMF therapy.

2. The conformable PEMF transducer of claim 1, wherein:
    said transducer coil further includes a secondary winding with a selected number of turns;

said activation electronics including an energy recovery circuit coupled to said secondary winding for recovering energy during each activation of said transducer.

3. The conformable PEMF transducer of claim 2, wherein:
said transducer coil is formed from winding layers including a primary/structural winding layer and at least one secondary winding layer;
said primary/structural winding layers including primary and structural windings, and said secondary winding layer including secondary windings.

4. The conformable PEMF transducer of claim 3, wherein two secondary winding layers are positioned on either side of said primary/structural winding bundle to form the transducer coil.

5. The conformable PEMF transducer of claim 2, wherein said energy recovery circuit includes an energy recovery capacitance coupled in parallel with said primary and secondary windings.

6. The conformable PEMF transducer of claim 1, wherein said transducer coil further includes a sense winding with a selected number of sense, turns, said sense winding being coupled to said activation electronics for providing a feedback indication of the PEMF output from said transducer.

7. The conformable PEMF transducer of claim 1, wherein said transducer coil has a substantially flat cross sectional profile.

8. The conformable PEMF transducer of claim 7, wherein said primary and secondary windings are flat wound.

9. The conformable PEMF transducer of claim 1, wherein said activation electronics comprises:
control electronics for providing control signals that control the PEMF activation of said transducer windings; and
drive electronics responsive to said control signals for providing a selected activation current through said transducer windings.

10. The conformable PEMF transducer of claim 9, wherein
said drive electronics is located at one end of the transducer coil and encapsulated in a potting material that also covers the adjacent portions of the transducer coil; and
said control electronics is included in a separate control electronics module and coupled to said encapsulated drive electronics by a cable.

11. The conformable PEMF transducer of claim 1, wherein said activation electronics includes:
a PEMF processor;
a PEMF program for controlling the activation of the electromagnetic fields, thereby implementing a PEMF therapy program.

12. The conformable PEMF transducer of claim 11, wherein said activation electronics includes a pulse circuit for providing, under control of the PEMF program, pulses that cause the energization and de-energization of the transducer, thereby activating the electromagnetic field.

13. The conformable PEMF transducer of claim 12, wherein said activation electronics collects appropriate data for monitoring the patient's use of the PEMF system and the course of the PEMF therapy.

14. The conformable PEMF transducer of claim 13, wherein said activation electronics generates clock and calendar data, and wherein said PEMF program collects clock and calendar data representative of the patient's use of the PEMF system.

15. The conformable PEMF transducer of claim 1, wherein the selected target area for PEMF therapy is the hip, and said transducer is configured with a corresponding anatomical contour for positioning around the patient's hip.

16. The conformable PEMF transducer of claim 15, further comprising a hip belt into which the transducer coil is inserted for positioning on the patient's hip.

17. A method of fabricating a conformable PEMF transducer system for providing PEMF therapeutic stimulation to a target area of a patient's body, comprising the steps;
winding at least a primary winding with a selected number of turns and a structural winding with a selected number of turns of semi-rigid stiffening wire around a mandrel to form a primary/structural winding bundle;
binding said primary and structural windings together and removing said primary/structural winding bundle from the mandrel;
forming said primary/structural winding bundle into a selected anatomical contour; and
coupling activation electronics to said transducer for selectively activating electromagnetic fields, thereby implementing a prescribed PEMF therapy.

18. The method of fabricating a conformable PEMF transducer of claim 17, further comprising the step of:
winding a secondary winding with a selected number of turns around the mandrel;
binding said secondary winding together and removing the secondary winding bundle from the mandrel; and
binding said secondary winding bundle and said primary/ structural winding bundle together to form the transducer coil;
said activation electronics including an energy recovery circuit coupled to said secondary winding for recovering energy during each activation of said transducer.

19. The method of fabricating a conformable PEMF transducer of claim 18, further comprising the steps of:
positioning at least a portion of said activation electronics at one end of the transducer coil; and
encapsulating said portion of said activation electronics and the adjacent portion of the transducer coil in a potting material.

20. The method of fabricating a conformable PEMF transducer of claim 17, wherein the step of winding primary and structural windings further includes winding a sense winding with a selected number of turns.

21. The method of fabricating a conformable PEMF transducer of claim 17, wherein the step of winding primary and structural windings is accomplished by winding around a substantially flat mandrel, such that the primary/structural winding bundle has a substantially flat cross sectional profile.

22. A conformable PEMF transducer for providing PEMF therapeutic stimulation to a selected area of a patient's body, comprising:
a primary/structural winding layer formed by a primary winding with a selected number of turns and a structural winding with a selected number of turns;
at least one secondary winding layer formed by a secondary winding with a selected number of turns;

said primary/structural winding layer and said secondary winding layer being bound together to form an integral transducer coil, with the structural winding providing structural support such that the transducer coil is formable to a selected anatomical contour and is flexibly conformable to accommodate patient movement;

activation electronics positioned adjacent a portion of the transducer coil and encapsulated along with such portion in a potting material;

said activation electronics being coupled to said primary winding for selectively activating electromagnetic fields in response to control signals, thereby implementing a prescribed PEMF therapy;

attachment means for attaching said transducer coil to the selected area of the patient's body; and a control electronics module including control electronics coupled to said drive electronics for providing said control signals.

23. The conformable PEMF transducer of claim 22, further including a battery pack for said control electronics such that said control electronics module, and therefore, the transducer, is portable.

* * * * *